(12) United States Patent
Hirano et al.

(10) Patent No.: US 9,927,453 B2
(45) Date of Patent: Mar. 27, 2018

(54) DISPENSING DEVICE AND DISPENSING METHOD (71) Applicant: HITACHI HIGH-TECHNOLOGIES CORPORATION, Tokyo (JP)

(72) Inventors: Masaaki Hirano, Tokyo (JP); Takamichi Mori, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 42 days.

(21) Appl. No.: 15/106,881

(22) PCT Filed: Jan. 22, 2015

(86) PCT No.: PCT/JP2015/051597
§ 371 (c)(1),
(2) Date: Jun. 21, 2016

(87) PCT Pub. No.: WO2015/136991
PCT Pub. Date: Sep. 17, 2015

(65) Prior Publication Data
US 2016/0341756 A1 Nov. 24, 2016

(30) Foreign Application Priority Data

Mar. 10, 2014 (JP) ................................ 2014-046704

(51) Int. Cl.
*G01N 35/10* (2006.01)
*B01L 3/00* (2006.01)
(Continued)

(52) U.S. Cl.
CPC .......... *G01N 35/1016* (2013.01); *B01L 3/021* (2013.01); *B01L 3/52* (2013.01);
(Continued)

(58) Field of Classification Search
CPC ....... B01L 2400/0487; B01L 2200/143; B01L 2200/146; G01N 2035/1044; G01N 35/1016; G01N 35/1079
See application file for complete search history.

(56) References Cited

U.S. PATENT DOCUMENTS 5,499,545 A    3/1996  Kimura et al.
5,969,272 A   10/1999  Tanaka
              (Continued)

FOREIGN PATENT DOCUMENTS

EP    0 747 689 A2   12/1996
JP    07-005014 A     1/1995
              (Continued)

OTHER PUBLICATIONS

Chinese Office Action received in corresponding Chinese Application No. 201580003441.X dated Nov. 7, 2016.
(Continued)

*Primary Examiner* — Brian R Gordon
(74) *Attorney, Agent, or Firm* — Mattingly & Malur, PC (57) ABSTRACT

In order to increase the accuracy of dispensing liquid from a sealed liquid holding container without increasing device complexity, pressures inside and outside the sealed liquid holding container are measured with a pressure sensor connected to a dispensing probe, and the amount of discharge operation of a pump is corrected in accordance with the measured pressures. The amount of operation of the pump is corrected by calculating the amount of deformation of a dispensing flow passageway due to pressure change.

4 Claims, 8 Drawing Sheets

(51) Int. Cl.
  *G01F 22/02* (2006.01)
  *B01L 3/02* (2006.01)
(52) U.S. Cl.
  CPC ......... *G01F 22/02* (2013.01); *G01N 35/1079* (2013.01); *B01L 2200/0673* (2013.01); *B01L 2200/143* (2013.01); *B01L 2200/146* (2013.01); *B01L 2400/0487* (2013.01)

(56) References Cited

U.S. PATENT DOCUMENTS

| | | | |
|---|---|---|---|
| 6,322,752 | B1 | 11/2001 | Siddiqui et al. |
| 2006/0263250 | A1 | 11/2006 | Blouin et al. |
| 2010/0273243 | A1 | 10/2010 | Oue et al. |
| 2011/0171744 | A1* | 7/2011 | Saegusa ............ G01N 35/1009 436/148 |
| 2012/0196374 | A1 | 8/2012 | Haga |
| 2014/0106467 | A1* | 4/2014 | Hutter .................... B01L 3/021 436/180 |
| 2014/0193918 | A1 | 7/2014 | Takahashi et al. |

FOREIGN PATENT DOCUMENTS

| | | |
|---|---|---|
| JP | 09-304400 A | 11/1997 |
| JP | 2004-020320 A | 1/2004 |
| JP | 2004-523434 A | 8/2004 |
| JP | 2009-156744 A | 7/2009 |
| JP | 2011-080964 A | 4/2011 |
| JP | 2013-054014 A | 3/2013 |
| JP | 2013-064751 A | 4/2013 |
| WO | 02/064492 A2 | 8/2002 |

OTHER PUBLICATIONS

Extended European Search Report received in corresponding European Application No. 15761890.1 dated Oct. 30, 2017.
International Search Report of PCT/JP2015/051597 dated Feb. 17, 2015.

* cited by examiner

DISPENSING DEVICE AND DISPENSING METHOD

TECHNICAL FIELD

The present invention relates to a liquid dispensing device, an automatic analysis device equipped with the same, and a liquid dispensing method, such as a dispensing method for collecting liquid from a liquid holding container, such as a sample container or a reagent container, and dispensing the liquid into a reaction container.

BACKGROUND ART

For example, automatic analysis devices generally employ an non-sealed liquid holding container with the upper opening portion opened. In recent years, use of sealed liquid holding containers with the opening portion closed with a rubber plug, such as a vacuum blood collection tube, have become widespread. In dispensing devices, too, there is a demand for direct liquid collection without having to unplug the sealed holding container.

However, the inside of a sealed liquid holding container typically has a negative pressure relative to the external atmospheric pressure. When a lid has been opened and closed, or if sample injection into the container has been performed using a syringe, for example, the internal pressure may have become positive relative to the external atmospheric pressure. When there is a pressure difference between the inside and outside of the liquid holding container, as a probe is inserted into the liquid holding container, the flow passageway of the dispensing device as a whole connected to the probe may contract or expand due to a pressure variation, causing a movement of the liquid or gas in the flow passageway. In addition, when the probe is removed from the liquid holding container, the flow passageway may be deformed again by exposure to the atmosphere, causing a movement of the liquid or gas in the flow passageway, including a suctioned sample. As a result, the position of the suctioned sample in the probe may vary due to different internal pressures of the liquid holding container. This makes it impossible to obtain a constant amount of dispensed liquid relative to the amount of operation of a pump, and to achieve required dispensing accuracy.

Various measures have been taken to eliminate the pressure difference between the inside and outside of the liquid holding container. For example, a probe is provided with a thin tube for liquid sample suction and a thin tube for ventilation that are integrated (see Patent Literature 1). According to this technology, the probe equipped with the two passageways is passed through the rubber plug, and ventilation is performed via the ventilation passageway while liquid is suctioned via the suction passageway, thus eliminating the pressure difference between the inside and outside of the liquid holding container. In another example, an insertion hole for the sample collection probe is formed in the sample container plug using a perforating device equipped with a Z-shaped blade (see Patent Literature 2). According to this technology, as the sample collection probe is inserted, the opening or hole formed in the plug expands, whereby sufficient ventilation is provided, eliminating the pressure difference between the inside and outside of the liquid holding container.

CITATION LIST

Patent Literature

Patent Literature 1: JP 9-304400 A
Patent Literature 2: JP 2004-523434 A

SUMMARY OF INVENTION

Technical Problem

In Patent Literature 1, the ventilation passageway is provided in addition to the suction passageway. As a result, the probe outer shape is increased, with a resultant increase in the frictional force experienced when piercing the rubber plug. Accordingly, a large force is required for probe removal or insertion. In addition, there is the potential problem of sample leakage and the like via the through-hole that may remain in the rubber plug after the probe is removed. In Patent Literature 2, because the perforating blade is used in addition to the sample collection probe, the device becomes more complex and the time and effort for maintenance, for example, increases. Further, in order to avoid cross contamination of samples, the perforating blade needs to be washed, resulting in an increase in the consumption of washing water.

The present invention was made in view of the above circumstances, and an object of the present invention is to provide a dispensing method that can increase the accuracy of dispensing liquid from a sealed liquid holding container without an increase in device complexity due to the provision of a ventilation opening.

Solution to Problem

According to the present invention, pressures inside and outside a sealed liquid holding container are measured, the amount of deformation of a dispensing flow passageway due to pressure variation is calculated, and the amount of operation of a pump is corrected in accordance with the amount of deformation.

Specifically, a dispensing device according to the present invention includes a pump; a probe connected to the pump via a piping; a pressure sensor that measures a pressure in the piping; and a control unit that controls the pump and the probe and that reads a signal from the pressure sensor. When a liquid is dispensed from a sealed container, the control unit measures pressures outside and inside the container using the pressure sensor, and corrects the amount of operation of the pump in accordance with the measured pressures.

The control unit may correct the amount of operation of the pump for discharging the liquid, or the amount of operation of the pump for suctioning or discharging air into or out of the probe.

A dispensing method according to the present invention includes a step of suctioning a segmented air into a probe; a step of measuring a pressure outside a sealed container; a step of measuring a pressure inside the container; a step of calculating a correction amount for a discharge amount required for discharging a liquid suctioned by the probe from the container, based on the measured external and internal pressures; a step of suctioning into the probe the liquid held in the container; a step of removing the probe from the container; and a step of discharging the suctioned liquid from the probe by applying the correction amount for the discharge amount.

A dispensing method according to the present invention includes a step of suctioning a segmented air into a probe; a step of measuring a pressure outside a sealed container; a step of inserting the probe into the container; a step of measuring a pressure inside the container; a step of discharging or suctioning the segmented air, based on the measured external and internal pressures, so that the amount of the segmented air becomes a predetermined amount with the probe removed from the container; a step of suctioning into the probe a liquid held in the container; a step of suctioning air from the container into a tip of the probe so that the air has a predetermined amount with the probe removed from the container; a step of removing the probe from the container; and a step of discharging the suctioned liquid from the probe.

Advantageous Effects of Invention

According to the present invention, the accuracy of dispensing liquid from a sealed liquid holding container can be increased without an increase in device complexity due to the provision of a ventilation opening.

Other problems, features, and effects will become apparent from the following description of embodiments.

DESCRIPTION OF EMBODIMENT

In the following, an embodiment of the present invention will be described with reference to the drawings.

Example 1

Figure 1:
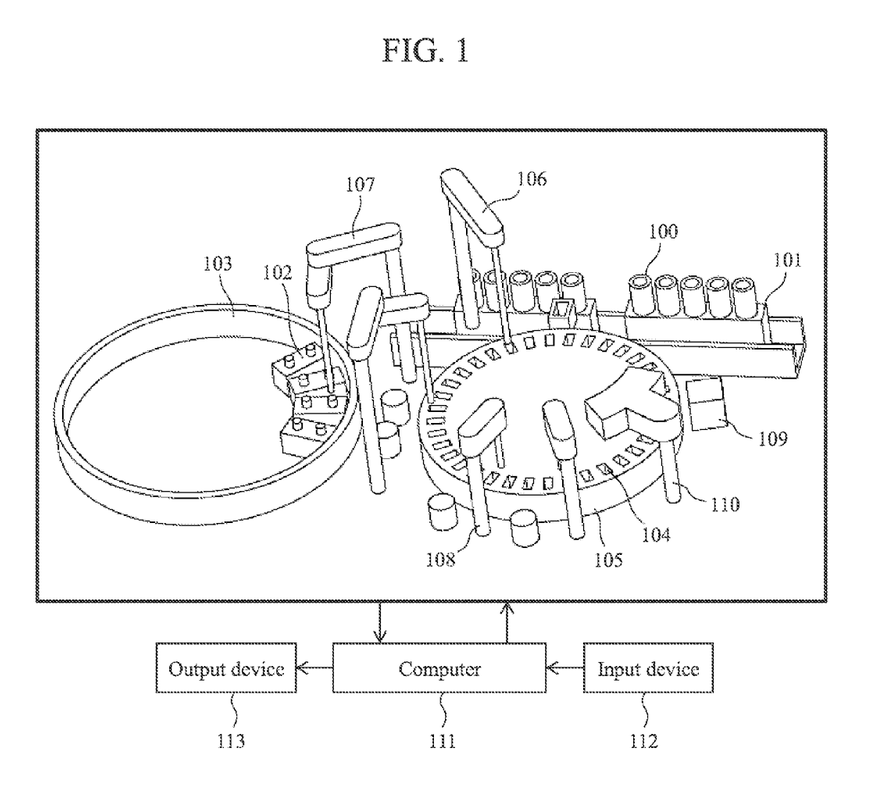
FIG. 1 is a schematic diagram illustrating an overall configuration example of an automatic analysis device.

An automatic analysis device is a device for automatically analyzing the components of a biological sample, such as blood or urine. The device includes a dispensing device for collecting and dispensing liquid from a sample container or a reagent container into a reaction container. FIG. 1 is a schematic diagram of an overall configuration example of the automatic analysis device. The automatic analysis device is provided with a sample rack 101 in which a plurality of sample containers 100 containing samples is disposed; a reagent disc 103 on which a plurality of reagent bottles 102 containing reagents is disposed; a cell disc 105 on which a plurality of reaction cells 104 for mixing sample and reagent into a reaction liquid is disposed; a sample dispensing mechanism 106 capable of moving a certain quantity of sample from within the sample containers 100 into the reaction cells 104; and a reagent dispensing mechanism 107 capable of moving a certain quantity of reagent from within the reagent bottles 102 into the reaction cells 104. The automatic analysis device is also provided with a stirring unit 108 for stirring and mixing the sample and reagent in the reaction cells 104; a measurement unit 109 for irradiating the reaction liquid in the reaction cells 104 with light and receiving resultant light; a washing unit 110 for washing the reaction cells 104; a computer 111 for controlling the driving of various parts of the analysis device, reading measurement data, and storing and analyzing data; an input device 112 capable of inputting necessary data into the computer 111 from the outside; and an output device 113 capable of displaying and outputting data to the outside.

An analysis of the amounts of components in a sample is performed by the following procedure. First, a certain quantity of a sample in the sample container 100 is dispensed into the reaction cell 104 by the sample dispensing mechanism 106. Then, a certain quantity of a reagent in the reagent bottle 102 is dispensed into the reaction cell 104 by the reagent dispensing mechanism 107. The sample and reagent in the reaction cell 104 are stirred by the stirring unit 108, producing a reaction liquid. If necessary, a plurality of reagents may be additionally dispensed into the reaction cell 104 by the reagent dispensing mechanism 107. During those dispensing processes, the sample container 100, the reagent bottle 102, and the reaction cell 104 are moved to predetermined positions by the transport of the sample rack 101 and rotation of the reagent disc 103 and the cell disc 105. After completion of the reaction, the inside of the reaction cell 104 is washed by the washing mechanism 110 for the next analysis. The absorbance of the reaction liquid is measured by the measurement unit 109, and absorbance data are accumulated in the computer 111. From the accumulated absorbance data, the computer 111 analyzes the component amounts on the basis of calibration curve data and the Lambert-Beer law. The data necessary for controlling various units and analysis are input from the input device 112 into the computer 111. Various data and analysis results are displayed and output by the output device 113.

Figure 2:
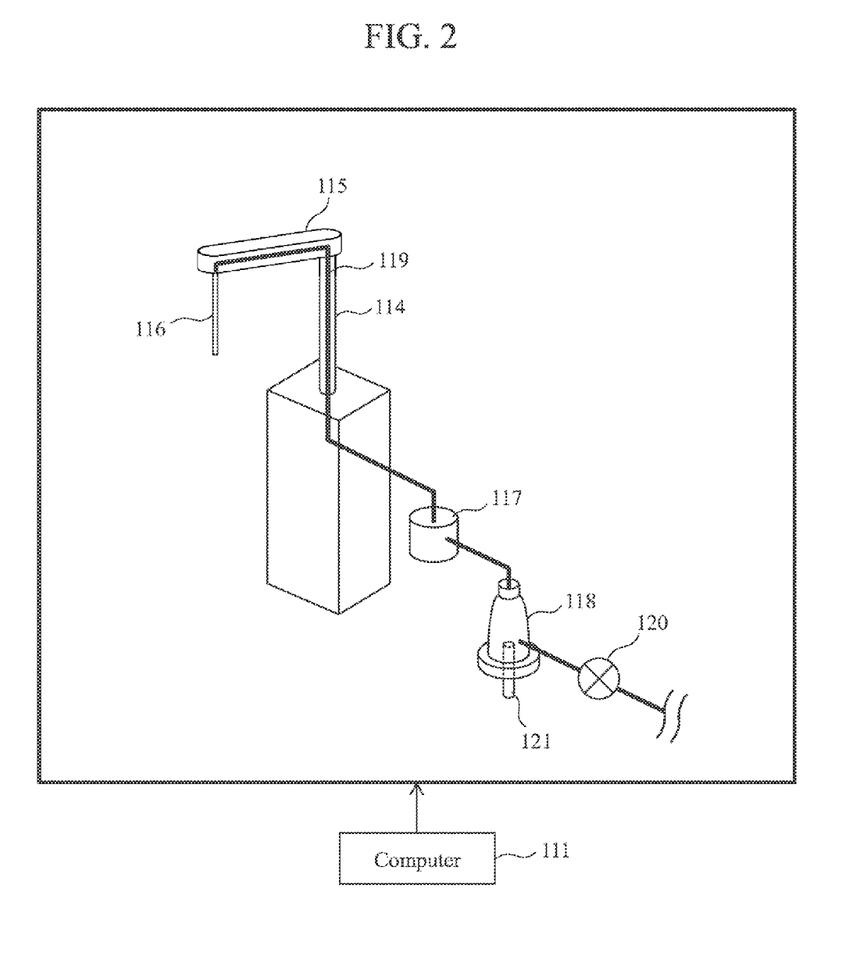
FIG. 2 is a schematic diagram illustrating a configuration example of a dispensing mechanism.

FIG. 2 is a schematic diagram of a configuration example of the dispensing mechanism. On a shaft 114 that can be driven up and down, an arm 115 that can be rotationally driven is installed. At the end of the arm 115, a dispensing probe 116 is installed. The dispensing probe 116, a pressure sensor 117, and a syringe pump 118 are connected via piping 119. The dispensing flow passageway has the distal side thereof opened via the dispensing probe 116, with the proximal side thereof being configured to be opened and closed by an electromagnetic valve 120. During liquid dispensing operation, the electromagnetic valve 120 is closed so as to suction or discharge the sample or reagent via the tip of the dispensing probe 116 by the movement of a plunger 121 installed in the syringe pump 118. After completion of the dispensing operation, the electromagnetic valve is opened to supply washing water from the proximal side.

As a comparative example, a conventional liquid sample dispensing sequence under the atmospheric pressure will be described with reference to a schematic diagram shown in FIG. 3.

Figure 3:
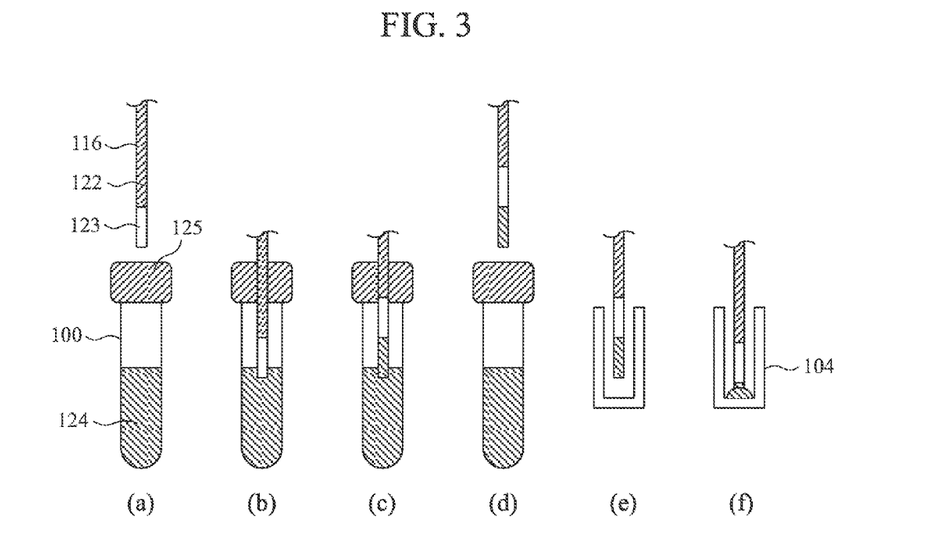
FIG. 3 is a schematic diagram illustrating a conventional liquid sample dispensing sequence under an atmospheric pressure.

FIG. 3(a) illustrates a sealed sample container 100 immediately prior to the insertion of the dispensing probe 116 therein. In this example, the pressure inside the sample container 100 is the same as the pressure outside the sample container 100, i.e., the atmospheric pressure. The dispensing probe 116 is filled with water 122 for transmitting the pressure from the syringe pump 118. Into the tip of the dispensing probe 116, segmented air 123 is suctioned in advance, thus forming an air layer for preventing the sample 124, as it is being suctioned, from being mixed with and diluted by the water 122. Thereafter, as illustrated in FIG. 3(b), the dispensing probe 116 is inserted into the sample container 100 via a rubber plug 125 until reaching inside the liquid of the sample 124. Then, as illustrated in FIG. 3(c), the sample 124 is suctioned into the dispensing probe 116. As illustrated in FIG. 3(d), the dispensing probe 116 is then removed out of the sample container 100. Finally, as illustrated in FIG. 3(e), the dispensing probe 116 is moved into the reaction cell 104, and the suctioned sample 124 is discharged into the reaction cell 104, as illustrated in FIG. 3(f).

Next, a dispensing sequence in the case where the inside of the sealed sample containers 100 is at negative pressure will be described with reference to a schematic diagram shown in FIG. 4. Also, the difference from the case where the sample container has the atmospheric pressure will be described with reference to FIG. 5 illustrating a temporal change in pressure in the dispensing flow passageway. In FIG. 5, illustrating the pressure variation in the dispensing flow passageway, the solid line indicates the case where the sample container has negative pressure, and the broken line indicates the case where the sample container has the atmospheric pressure.

Figure 4:
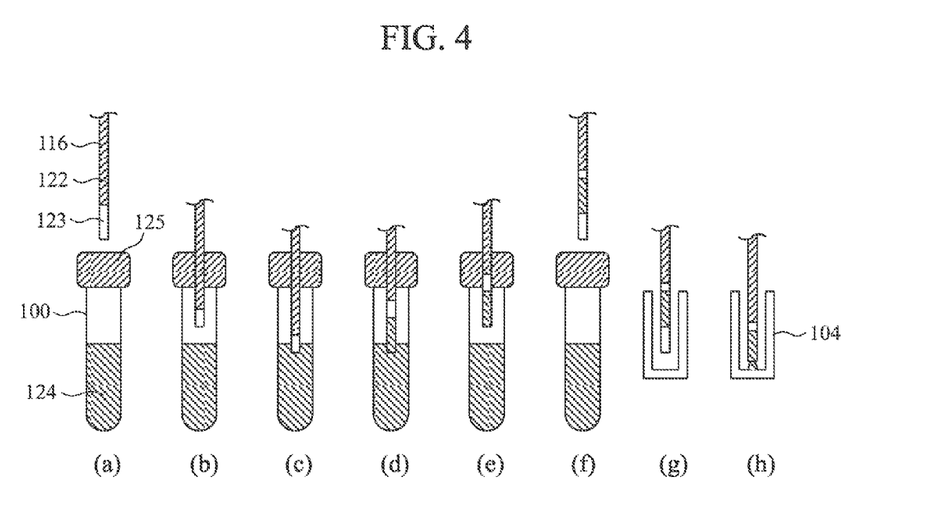
FIG. 4 is a schematic diagram illustrating a liquid sample dispensing sequence under a negative pressure.
Figure 5:
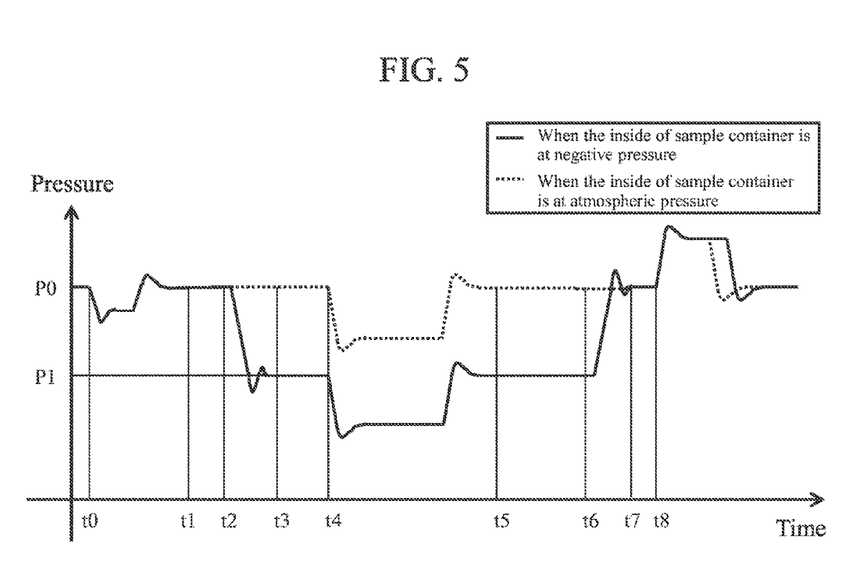
FIG. 5 is a diagram illustrating a temporal change in dispensing route pressure.

FIG. 4(a) illustrates the dispensing probe 116 filled with the water 122, with the segmented air 123 suctioned therein. As the segmented air 123 is suctioned, the pressure in the dispensing flow passageway decreases during the suction operation, as illustrated in the pressure data of FIG. 5 between times t0 to t1. As the dispensing probe 116 is inserted into the sample container 100 as illustrated in FIG. 4(b), the dispensing flow passageway and the sample container 100 are hermetically connected. When the inside of the reagent container 100 is at the atmospheric pressure, no change is caused in the pressure in the dispensing flow passageway, as illustrated in the pressure data of FIG. 5 between times t2 and t3. However, in the case of negative pressure, the pressure decreases from P0 to P1. As a result, the dispensing flow passageway contracts as a whole, and the interface of the water 122 in the dispensing probe 116 moves toward the sample container 100, whereby the volume of the segmented air 123 in the dispensing probe 116 decreases.

Then, as illustrated in FIG. 4(c), the dispensing probe 116 reaches the sample 124 in the sample container 100, and the sample 124 is suctioned into the dispensing probe 116, as illustrated in FIG. 4(d). At this time, the pressure in the dispensing flow passageway decreases during the suction operation, as illustrated in FIG. 5 between time t4 to t5. Thereafter, as illustrated in FIG. 4(e) to (f), as the dispensing probe 116 is removed out of the sample container 100, the hermetic connection of the dispensing flow passageway and the sample container 100 is released. At this time, if the inside of the sample container 100 is at the atmospheric pressure, no change is caused in the pressure of the dispensing flow passageway, as illustrated in the pressure data of FIG. 5 from time t6 to t7. However, if the internal pressure is negative, the pressure in the dispensing flow passageway is exposed to the atmosphere and turns from P1 to P0. As a result, the flow passageway as a whole expands, whereby the interface of the water 122, the segmented air 123, and the sample 124 in the dispensing probe 116 are moved from the tip toward the proximal side, and air enters the tip of the dispensing probe 116. Finally, as illustrated in FIG. 4(g), the dispensing probe 116 is moved into the reaction cell 104, and the suctioned sample 124 is discharged into the reaction cell 105 as illustrated in FIG. 4(h). When the inside of the sample container 100 is at negative pressure, the discharge amount relative to the amount of operation of the pump becomes insufficient because of the entry of air into the tip.

Accordingly, in the present example, in order to eliminate the lack of discharge amount, the amount of discharge operation is corrected in accordance with the pressure in the sealed sample container 100. A sequence of the present example will be described with reference to a flowchart shown in FIG. 6 and a schematic diagram shown in FIG. 7.

Figure 6:
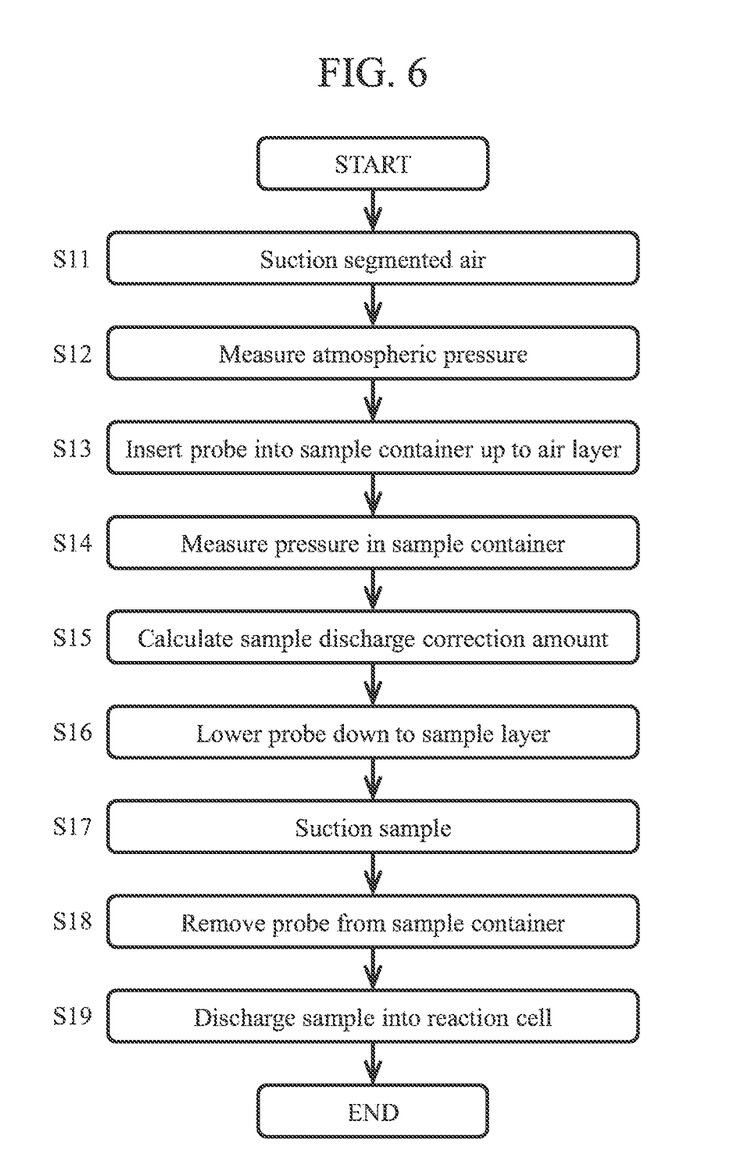
FIG. 6 is a flowchart of a dispensing sequence in which the sample discharge amount is corrected in accordance with pressure.
Figure 7:
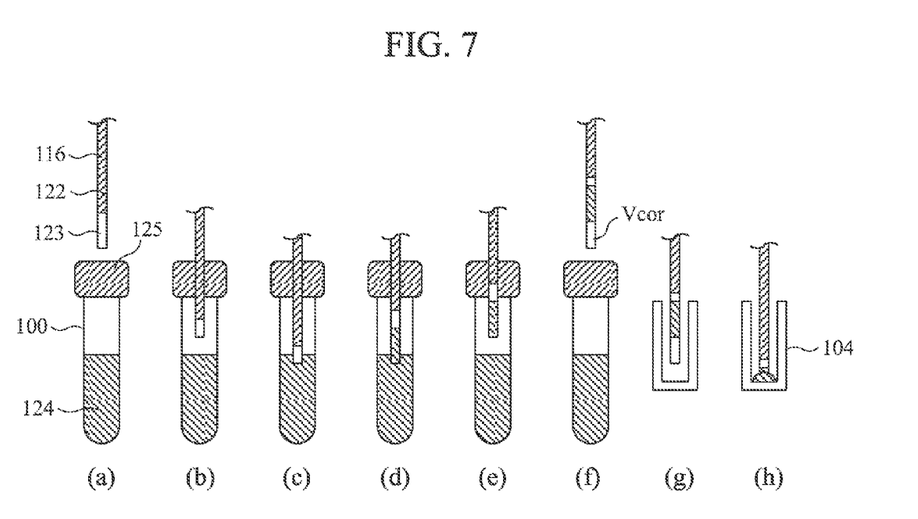
FIG. 7 is a schematic diagram of the dispensing sequence in which the sample discharge amount is corrected in accordance with pressure.

Referring to FIG. 6, after the start of the dispensing operation, the segmented air 123 is suctioned in step 11 (FIG. 7(a)). In step 12, the atmospheric pressure is measured. This is performed at time t1 in FIG. 5, whereby the atmospheric pressure P0 is obtained. In step 13, the dispensing probe 116 is inserted via the rubber plug 125 into the air layer in the sealed sample container 100 (FIG. 7(b)). In step 14, the pressure inside the sample container 100 is measured. This step is performed at time t3 in FIG. 5, whereby pressure P1 is obtained. The atmospheric pressure P0 outside the sample container 100 and the internal pressure P1 having been acquired, a sample discharge correction amount is calculated in step 15. A method for calculating the correction amount will be described later.

Thereafter, in step 16, the dispensing probe 116 is lowered to the sample layer (FIG. 7(c)), and the sample 124 is suctioned in step 17 (FIG. 7(d)). In step 18, as the dispensing probe 116 is removed from the sample container 100, the pressure in the dispensing flow passageway is opened to the atmospheric pressure, and air enters the tip of the dispensing probe 116, as illustrated in FIG. 7(f). Finally, the dispensing probe 116 is inserted into the reaction cell 104 (FIG. 7(g)), and the sample 124 is discharged into the reaction cell 104 in step 19 by applying the sample discharge correction amount obtained in step 15 in consideration of the lack due to the entry of air (FIG. 7(h)), and the sequence ends.

While the example has been described in which the atmospheric pressure P0 is measured at time t1 in FIG. 5, a similar result will be obtained when the measurement is conducted between times t7 and t8 in which the dispensing probe 116 is removed from the sample container 100. Alternatively, the measurement may be conducted at both timings to obtain an average so as to effectively increase the pressure measurement accuracy. Also, the pressure inside the sample container 100 may be measured between t5 and t6 rather than at time t3 in FIG. 5, or at both timings. In addition, while the example has been described in which the dispensing probe 116 is lowered to the air layer of the sample container 100 in step 13, and the pressure measurement is conducted in step 14 when the lowering is stopped, the pressure measurement may be conducted during the lowering as long as the measurement is not affected by vibrations and the like during operation. Further, if there is sufficient time for a pressure variation to become stabilized after the dispensing probe 116 is inserted into the sample container 100 and before reaching the sample layer, the dispensing probe 116 may not be stopped at the air layer but may be continuously lowered. The pressure measurement is also possible with the dispensing probe 116 immersed in the sample layer.

A method for calculating the sample discharge correction amount from the atmospheric pressure P0 outside the sample container 100 and the internal pressure P1 will be described. The lack of discharge amount due to the pressure change corresponds to the amount of air $V_{cor}$ that has entered the tip of the dispensing probe 116 as illustrated in FIG. 7(*f*), and is caused by deformation of the dispensing flow passageway and a volume change in the segmented air 123. Accordingly, the correction amount can be determined by calculating the relevant amounts of change.

As illustrated in FIG. 2, the dispensing flow passageway includes the dispensing probe 116, the pressure sensor 117, the syringe pump 118, and the piping 119 connecting them. For example, the piping 119 is cylindrical and has an inner diameter $r_{in}$, an outer diameter $r_{out}$, a length l, a Young's modulus E, and a Poisson's ratio v. When the piping 119 is subjected to internal pressure $P_{in}$ and external pressure $P_{out}$, the amount of change in inner diameter $\Delta r_{in}$ and the amount of change in length $\Delta l$ can be computed as follows:

$$\Delta r_{in} = \frac{r_{in}}{E}\left\{\left(v + \frac{r_{out}^2 + r_{in}^2}{r_{out}^2 - r_{in}^2}\right)P_{in} - \frac{2r_{out}^2}{r_{out}^2 - r_{in}^2}P_{out}\right\}$$

$$\Delta l = \frac{vl}{E}\left(-\frac{2r_{in}^2}{r_{out}^2 - r_{in}^2}P_{in} + \frac{2r_{out}^2}{r_{out}^2 - r_{in}^2}P_{out}\right)$$

When the dispensing probe 116 is inserted in the sample container 100, $P_{out}$=P0 and $P_{in}$=P1, so that both $\Delta r_{in}$ and $\Delta l$ can be derived. Accordingly, the amount of deformation $\Delta V_{tube}$ of the piping 119 can be calculated as follows:

$$\Delta V_{tube} = \pi\{(r_{in} + \Delta r_{in})^2(l + \Delta l) - r_{in}^2 l\}$$

By calculating the above for all of the constituent components and summing the results, the amount of deformation $\Delta V_{fc}$ of the flow passageway as a whole is determined. Then, a change in volume of the segmented air 123 is determined. When the suctioned amount of the segmented air 123 is $V_{air}$, and in view of the fact that the amount of deformation $\Delta V_{fc}$ of the piping when the dispensing probe 116 is inserted into the sample container 100 corresponds to the amount of leakage of the segmented air 123, the amount of volume change $\Delta V_{air}$ due to pressure at the time of removal can be calculated as follows:

$$\Delta V_{air} = \frac{P1 - P0}{P0}(V_{air} + \Delta V_{fc})$$

From the above calculation results, the eventual sample discharge correction amount $V_{cor}$ and the discharge amount $V_{dspc}$ after correction (the discharge amount before correction: $V_{dsp}$) can be determined as follows:

$$V_{cor} = -(\Delta V_{fc} + \Delta V_{air})$$

$$V_{dspc} = V_{dsp} + V_{cor}$$

These computations may be performed in real time during the sequence based on the pressure measurement results. Alternatively, data about the relationship between pressure and correction amount may be stored in advance, and a corresponding correction amount may be read based on a pressure measurement result.

Example 2

In this example, a method for correcting the amount of the segmented air 123 and the discharge amount will be described.

As illustrated in FIG. 4, the amount of the segmented air 123 varies depending on the pressure inside the sealed sample container 100. The segmented air 123 serves to prevent the sample from being diluted by the entry of the water 122, which transmits the pressure from the syringe pump, into the suctioned sample. However, dilution may not be completely avoided, and the way the sample is diluted may differ depending on the amount of the segmented air. In addition, when the sample 124 is suctioned, the segmented air 123 may expand or contract, and the time between the end of suctioning and pressure stabilization may be greatly influenced by the expansion or contraction, depending on the viscosity of the sample. For any of these problems, it is effective to perform correction so that the amount of the segmented air 123 becomes constant regardless of the pressure inside the sample container 100.

Figure 8:
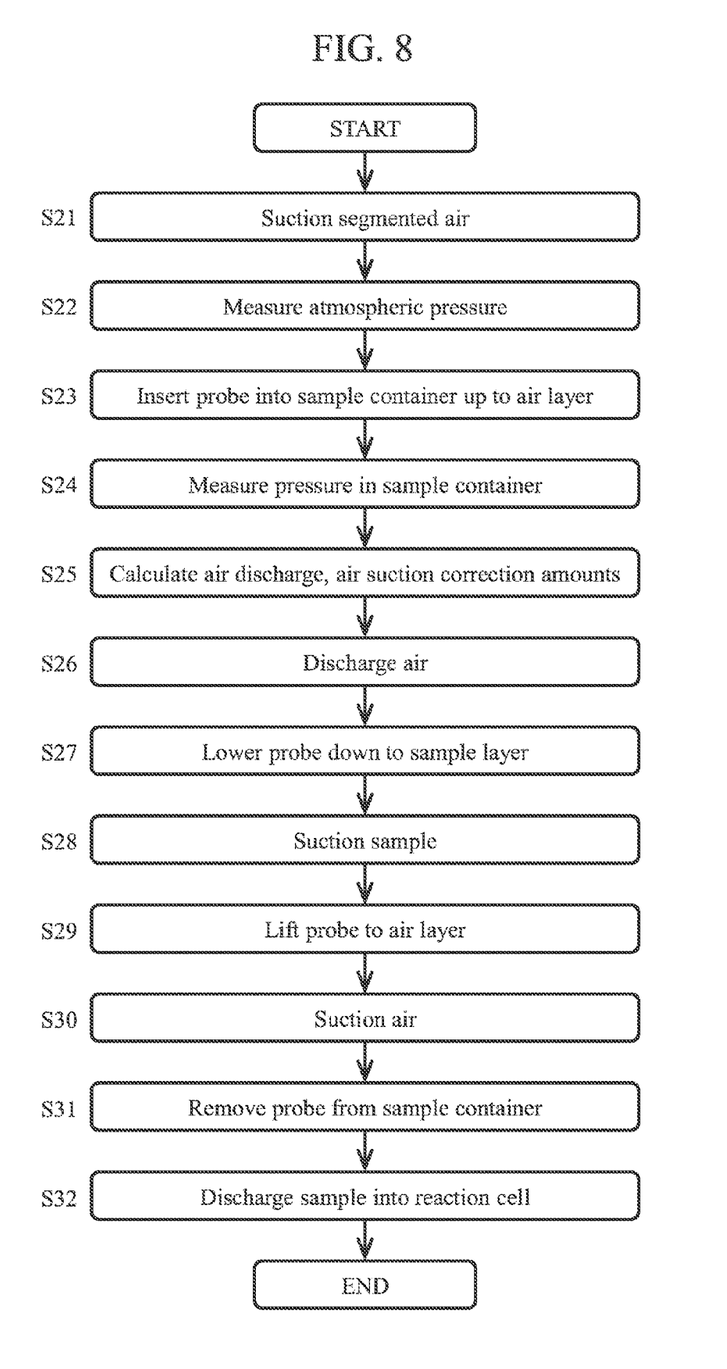
FIG. 8 is a flowchart of a dispensing sequence in which the segmented air amount is corrected in accordance with pressure.

An example of a dispensing sequence involving a pump operation correction for achieving a constant amount of the segmented air 123 will be described with reference to a flowchart shown in FIG. 8 and a schematic diagram shown in FIG. 9.

Figure 9:
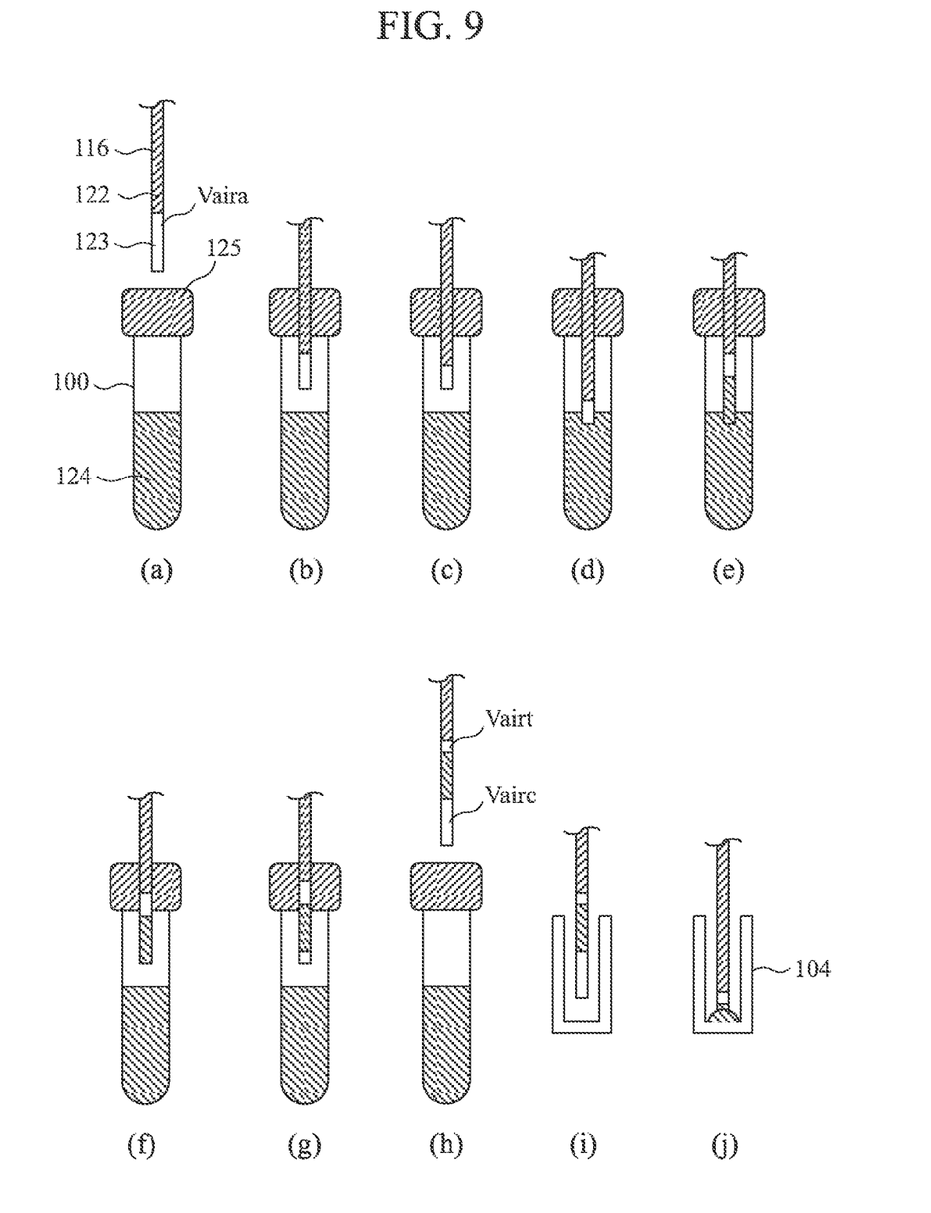
FIG. 9 is a schematic diagram of the dispensing sequence in which the segmented air amount is corrected in accordance with pressure.

After the start of the dispensing operation, the segmented air 123 is suctioned in step 21 (FIG. 9(*a*)). At this time, a greater amount of segmented air 123 than will eventually be held in the dispensing probe 116 is suctioned to allow for the adjustment by the correction operation. Then, in step 22, the atmospheric pressure is measured. This is performed at time t1 in FIG. 5, whereby the atmospheric pressure P0 is obtained. In step 23, the dispensing probe 116 is inserted via the rubber plug 125 into the air layer of the sealed sample container 100 (FIG. 9(*b*)), and the pressure inside the sample container 100 is measured in step 24. This step is performed at time t3 in FIG. 5, whereby pressure P1 is obtained. The atmospheric pressure P0 outside the sample container 100 and the internal pressure P1 having been acquired, air discharge and air suction correction amounts are calculated in step 25. A method for calculating the correction amounts will be described later. In step 26, an air discharge operation is performed by applying the result of the correction amount calculation in step 25 so as to achieve a constant amount of the segmented air 123 (FIG. 9(*c*)).

Thereafter, in step 27, the dispensing probe 116 is lowered to the sample layer (FIG. 9(*d*)), and the sample 124 is suctioned in step 28 (FIG. 9(*e*)). This is followed by lifting the dispensing probe 116 up to the air layer in step 29 (FIG. 9(*f*)), and an air suction operation is performed in step 30 by applying the result of the correction amount calculation in step 25 in consideration of the amount of air that enters the tip when the pressure in the dispensing flow passageway returns to the atmospheric pressure (FIG. 9(*g*)). Further, as the dispensing probe 116 is removed from the sample container 100 in step 31 (FIG. 9(*h*)), the internal pressure of the dispensing flow passageway is opened to the atmospheric pressure, allowing air to enter the tip of the dispensing probe 116, as described above. If the inside of the sample container 100 is at positive pressure, as the positive pressure is opened to the atmospheric pressure, the dispensing flow passageway will contract and the sample 124 may leak from the dispensing probe 116. However, when the air suction operation has been performed in consideration of the amount of deformation of the dispensing flow passageway in step 30, the leakage of the sample 124 can also be avoided.

Accordingly, at the end of step 31, the sample 124 can be held at a constant position in the dispensing probe 116 regardless of the pressure inside the sample container 100. Finally, the dispensing probe 116 is inserted into the reaction cell 104 (FIG. 9(i)), the sample 124 is discharged into the reaction cell 104 in step 32 (FIG. 9(j)), and the sequence ends. While in the foregoing example, the discharge operation is performed in step 26, a suction operation may be performed instead, given that the purpose is to make the amount of the segmented air 123 constant in accordance with the pressure inside the sample container 100. Whether a suction or discharge operation is performed may be selected depending on the pressure.

A method for calculating the air discharge/suction correction amount from the atmospheric pressure P0 outside the sample container 100 and the internal pressure P1 will be described. As described above, the difference in the amount of the segmented air 123 or the position of the suctioned sample due to pressure is caused by the deformation of the dispensing flow passageway and a volume change in the segmented air 123. The amount of deformation $\Delta V_{fc}$ of the dispensing flow passageway can be calculated from the physical property values and sizes of the flow passageway constituent elements and the pressure applied, as described with reference to Example 1.

A method for calculating the corrected discharge amount $V_{cor1}$ in step 26 of FIG. 8 will be described. When the suctioned amount of the segmented air 123 in step 21 is $V_{aira}$ (FIG. 9(a)) and the target amount of the segmented air 123 being held after removal of the dispensing probe 116 from the sample container 100 is $V_{airt}$ (FIG. 9(h)), the corrected discharge amount can be determined as follows:

$$V_{cor1} = V_{aira} + \Delta V_{fc} - V_{airt} \frac{P0}{P1}$$

A method for calculating the corrected suctioned amount $V_{cor2}$ in step 30 will be described. In order to control the amount of air being held under the sample 124 in the dispensing probe 116 after removal of the dispensing probe 116 from the sample containers 100 to become $V_{airc}$ (FIG. 9(h)), the corrected suctioned amount $V_{cor2}$ is set as follows:

$$V_{cor2} = V_{airc} + \Delta V_{fc} + V_{airt} \frac{P1 - P0}{P1}$$

Then, when sample discharge is performed in step 32, the sum of the amount of air $V_{airc}$ being held in the tip of the dispensing probe 116 and the amount of sample to be discharged into the reaction cell 105 is set as the amount of operation of the pump. The results of these calculations are also valid whether the pressure inside the sample container 100 is the atmospheric pressure, negative pressure, or positive pressure.

The present invention is not limited to the foregoing examples, and may include various modifications. The examples have been described for facilitating an understanding of the present invention, and are not necessarily limited to be provided with all of the described features. Some of the features of one example may be substituted by features of another example, or a feature of the other example may be added to the features of the one example. With respect to some of the features of each example, addition of another feature, deletion, or substitution may be made.

REFERENCE SIGNS LIST

100 Sample container
104 Reaction cell
114 Shaft
115 Arm
116 Dispensing probe
117 Pressure sensor
118 Syringe pump
119 Piping
120 Electromagnetic valve
121 Plunger
122 Water
123 Segmented air
124 Sample
125 Rubber plug

The invention claimed is:

1. A dispensing device comprising:
a pump;
a probe connected to the pump via a piping;
a pressure sensor that measures a pressure in the piping; and
a control unit configured to control the pump and the probe and to read a signal from the pressure sensor,
wherein the control unit is programmed to:
read a first signal from the pressure sensor to measure a first pressure while the probe is outside of a sealed container containing a liquid,
control the probe to insert the probe into the sealed container containing the liquid,
read a second signal from the pressure sensor to measure a second pressure inside of the sealed container while the probe is inserted in the sealed container,
calculate a correction amount of operation of the pump based on the measured first pressure and measured second pressure,
control the pump to suction the liquid from the sealed container, and
control the pump to discharge the suctioned liquid into a reaction container by operating the pump based on the calculated correction amount.

2. The dispensing device according to claim 1,
wherein the control unit is programmed to:
control the pump to discharge air by operating the pump based on the calculated correction amount, and
control the pump to suction air by operating the pump based on the calculated correction amount.

3. The dispensing device according to claim 1, wherein the control unit is programmed to:
calculate an amount of deformation of the piping due to a pressure change, and corrects the amount of operation of the pump based on the amount of deformation.

4. An automatic analyzer, comprising:
a reaction cell;
a sealed container containing a liquid;
a pump;
a probe connected to the pump via a piping;
a pressure sensor configured to measure a pressure in the piping;
a control unit configured to control the pump and the probe and to read a signal from the pressure sensor,
wherein the control unit is programmed to:

read a first signal from the pressure sensor to measure a first pressure while the probe is outside of the sealed container containing the liquid, control the probe to insert the probe into the sealed container containing the liquid, read a second signal from the pressure sensor to measure a second pressure inside of the sealed container while the probe is inserted in the sealed container, calculate a correction amount of operation of the pump based on the measured first pressure and measured second pressure, control the pump to suction the liquid from the sealed container, control the pump to discharge the suctioned liquid into a reaction container by operating the pump based on the calculated correction amount.

\* \* \* \* \*